US007711412B2

(12) United States Patent
Long

(10) Patent No.: US 7,711,412 B2
(45) Date of Patent: May 4, 2010

(54) MUCOSAL TISSUE ILLUMINATOR AND METHOD FOR USE

(75) Inventor: Gary L. Long, Cincinnati, OH (US)

(73) Assignee: Ethicon Endo-Surgery, Inc., Cincinnati, OH (US)

( * ) Notice: Subject to any disclaimer, the term of this patent is extended or adjusted under 35 U.S.C. 154(b) by 386 days.

(21) Appl. No.: 11/752,536

(22) Filed: May 23, 2007

(65) Prior Publication Data

US 2008/0294009 A1    Nov. 27, 2008

(51) Int. Cl.
*A61B 17/34*    (2006.01)
(52) U.S. Cl. .................. 600/476; 600/477; 600/478; 600/479
(58) Field of Classification Search .......... 600/421, 600/423, 476, 478, 466, 467, 471, 461
See application file for complete search history.

(56) References Cited

U.S. PATENT DOCUMENTS

| 6,234,955 | B1* | 5/2001 | Silverman et al. ............. 600/29 |
| 2002/0115918 | A1* | 8/2002 | Crowley ..................... 600/310 |
| 2005/0203561 | A1 | 9/2005 | Palmer et al. |
| 2005/0203562 | A1 | 9/2005 | Palmer et al. |
| 2005/0240147 | A1* | 10/2005 | Makower et al. ......... 604/96.01 |

\* cited by examiner

*Primary Examiner*—Long V Le
*Assistant Examiner*—Joel F Brutus
(74) *Attorney, Agent, or Firm*—Porter Wright Morris & Arthur LLP

(57) ABSTRACT

An illuminating system scatters light into the mucosal lining of the stomach adjacent to an ulcerated area, an area containing a lesion, or ather area of interest. A light detector positioned on the opposite side of the area of interest uses detected light patterns to identify the location of circulatory structures beneath the mucosal lining adjacent to the area of interest.

17 Claims, 3 Drawing Sheets

MUCOSAL TISSUE ILLUMINATOR AND METHOD FOR USE

TECHNICAL FIELD AND INDUSTRIAL APPLICABILITY OF THE INVENTION

The invention relates generally to into endoscopic surgery and more particularly to a method and apparatus for identifying sub-mucosal structures during endoscopic surgery. The invention will be specifically disclosed in connection with an apparatus for transillumination of the stomach tissue during endoscopic procedure.

BACKGROUND OF THE INVENTION

Peptic ulcers remain one of the commonest causes of acute upper gastrointestinal bleeding. In the past few years, significant progress has been made in the treatment of ulcer hemorrhage, particularly with the increasing development of endoscopic treatments. One method for treating ulcer hemorrhage is endoscopic haemostasis with a thermal probe. When an ulcerated area is observed in the stomach through an endoscope, for example, an RF or other type of thermal probe is applied against the ulcerated area through an endoscope. The thermal probe heats and coagulates the tissue to stop the actual or potential bleeding. To successfully perform a haemostasis, or to prevent future bleeding with a thermal probe, it frequently is necessary to coagulate tissue adjacent to the ulcerated areas visible through an endoscope.

The entire blood vessel needing to be coagulated for successful treatment of a bleeding, or potentially bleeding, ulcer generally is not fully visible through an endoscope. Part of the blood vessel needing to be coagulated generally is underneath the adjacent areas of stomach lining, and it coagulation of this portion of the blood vessel is performed by applying the thermal probe against the mucosal tissue in the stomach above the vessel, coagulating both the vessel and the mucosal tissue. For this reason, the physician applying the thermal probe is often forced to select the specific areas of the tissue to coagulate without full information about the circulatory and other structures underlying the stomach tissue surrounding the all selected areas. Even when the stomach ulcer is visibly actively bleeding at a specific location or when a portion of a blood vessel is visible through an endoscope at a specific location, the physician often lacks full information about the precise location of the remaining portions of the blood vessel needing to be coagulated, which remaining portions are located beneath the stomach lining in the vicinity of the bleeding. Due to these limitations, the physician cannot, as a practical matter, treat an ulcerated condition without also treating visually inaccessible portions of the blood vessel underlying the surrounding stomach tissue that are selection without adequate locating information. Hence, most successful haemostasis procedures with thermal probes heat and destroy not only the blood vessels requiring coagulation, but healthy surrounding tissue that do not need coagulation as well. Indeed, overtreating the area by coagulating portions of the adjacent area that do not need coagulating is the only practical way in the prior art in which the physician can be confident that the entire portion of the blood vessel needing coagulation is properly coagulated. The result of applying a thermal probe to areas not requiring coagulating is, of course, destroying healthy tissue and/or needlessly compromising circulation of blood to substantial areas of the stomach.

It is not uncommon for peptic ulcers to stop bleeding spontaneously, and it is often difficult to predict whether a clotted, non-active site that experienced recent stigmatic bleeding will rebleed, or whether visible blood vessel in a ulcer crater requires the intervention of a thermal probe to coagulate the tissue. For these reasons, decisions as to whether to treat such sites with an endoscopic thermal probe, or to treat the sites with proton pump inhibitors, are frequently controversial. One factor that greatly complicates that diagnostic and treatment decision is the inability of the physician to see or otherwise obtain information about circulatory structures beneath the stomach lining, particularly in those areas adjacent to ulcerated areas of the stomach. Hence, there is substantial need for information about the circulatory structures in these heretofore visually inaccessible areas beneath the stomach lining.

SUMMARY OF THE INVENTION

One example of the invention is a method of identifying structures proximal to ulcerated areas of the stomach. The method uses an endoscope to identify an ulcerated area in the mucosal lining of a patient's stomach. Light is then scattered from a light source into the mucosal lining of the stomach at a location adjacent to, and on a first side of, the identified area. A light detector is positioned on a second side of the identified area opposite to the first side. Light is directed from the light source into the mucosal lining toward the second side of the identified area. With the light detector positioned on the second side of the identified area, the light detector is used to detect patterns of light representative of positional attributes of structures within the identified area that are created by light emanating from the light source on the first side of the identified area and scattered in its travel through the mucosal lining. The detected light patterns are then used to determine positional attributes of the structures within the identified area and to treat ulcers in the identified area.

According to another example of the invention, the step of scattering light includes inserting a light source into the mucosal lining.

In another example of the invention, the step of scattering the light includes pressing a light source against the mucosal lining of the stomach.

In yet another example of the invention, the step of scattering the light includes positioning a light source in close proximity to the mucosal lining of the stomach.

According to another example of the invention, the light source is positioned close enough to the mucosal lining of the stomach to substantially eliminate reflectance of light waves from the light source.

The invention further includes a system for visually ascertaining attributes of structures located beneath mucosal linings of the stomach. An elongated shaft is configured for passage through a working channel of an endoscope. A light source is disposed proximal to the end of the elongated shaft. The light source is adapted for contact with mucosal lining of the stomach and capable of directing light with sufficient luminous intensity to pass through mucosal linings of the stomach in a predetermined direction. A light detector for detecting scattered patterns of light and producing an image representative of the patterns is then used to ascertain positional attributes of blood circulatory structures within the mucosal lining from the differential intensity of light passing through portions of the mucosal lining from the light source due to attenuation of the light by the circulatory structures.

In another example of the invention, the light source is disposed in the shaft, and the shaft includes a window for directing light emanating from the light source.

In another example of the invention, the shaft has a generally cylindrical configuration with the window being disposed in the circumferential section of the shaft.

BRIEF DESCRIPTION OF THE DRAWINGS

While the invention concludes with claims which particularly point out and distinctly claim the invention, it is believed the present invention will be better understood from the following description taken in conjunction with the accompanying drawings, in which like reference numbers identify the same elements in which:

Reference will now be made in detail to certain exemplary embodiments of the invention, examples of which are illustrated in the accompanying drawings.

DETAILED DESCRIPTION OF THE PREFERRED EMBODIMENTS OF THE INVENTION

Figure 1:
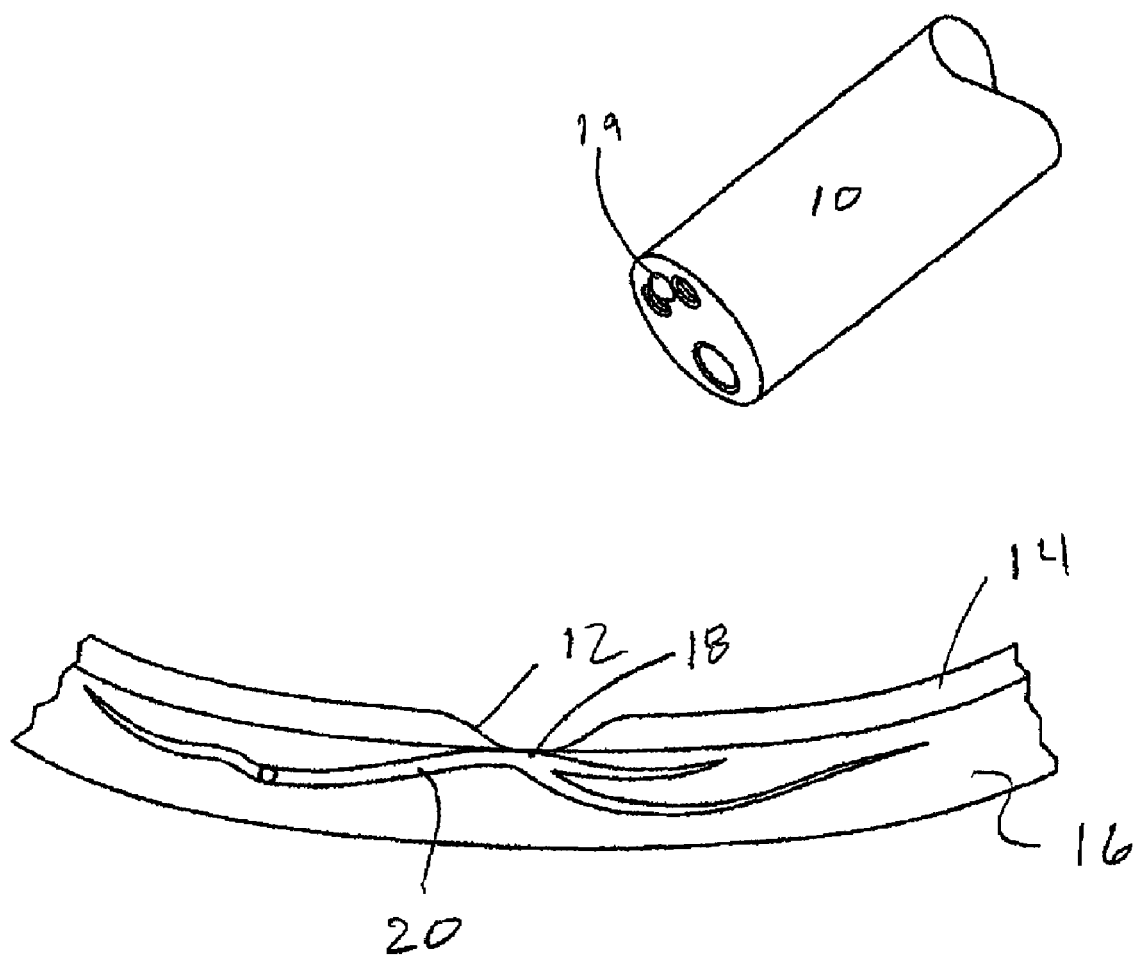
FIG. 1 is a schematic view of the end of an endoscope positioned in the stomach of a patient in proximity to an ulcer crater in the stomach lining, and showing blood vessels partially visible and partially visually obscured by the endoscope.

Referring now to the drawings, FIG. 1 shows an endoscope 10 positioned within a patient's stomach in close proximity to an eroded area 12 in the mucosa 14 of the stomach wall 16. The eroded area 12 partially exposes a portion 18 of a blood vessel 20, which portion 18 is visually detectable through an image sensor 20 located in the distal end of the endoscope 10. As illustrated in the exemplary embodiment of FIG. 1, visual detection of the eroded portion 12 by the image sensor 19 is aided by a light delivery system 22, also disposed in the distal end of the endoscope 10.

In order to successfully treat the eroded area 12, it may be necessary not only to coagulate or otherwise treat the exposed portion 18 of the blood vessel 20, but also to treat the portion of the blood vessel 20 that is obscured by the non-eroded or only partially eroded portions of the mucosal lining 14. Unfortunately, the light emitted from the light delivery system 22 of the endoscope 10 typically is predominately reflected by the mucosal lining 14, and generally is inadequate to reveal those portions of the blood vessel 20 adjacent to eroded area 12, i.e., those portions of the blood vessel 20 underlying the non-eroded or partially eroded areas of the lining 14. Consequently, the portions of the blood vessel 20 adjacent to the eroded area 12 typically are not visible to the physician with the light emitted from a typical endoscope light delivery system, such as the light delivery system 22 of the endoscope 10 in the specifically illustrated exemplary embodiment. Thus, even though a successful ulcer hemorrhage may require coagulation of portions of the blood vessel 20 beneath the areas of the mucosal lining 14 adjacent to the eroded area 18, the physician often lacks adequate information about the precise location of those portions of the blood vessel 20. Without precise locational information concerning the underlying circulatory system adjacent to the eroded area 18, it often is necessary, in order to completely stop bleeding at the site, for a physician to coagulate (or otherwise treat) an area of the mucosal lining 14 that is larger than necessary, thereby unnecessarily destroying healthy tissue.

Figure 2:
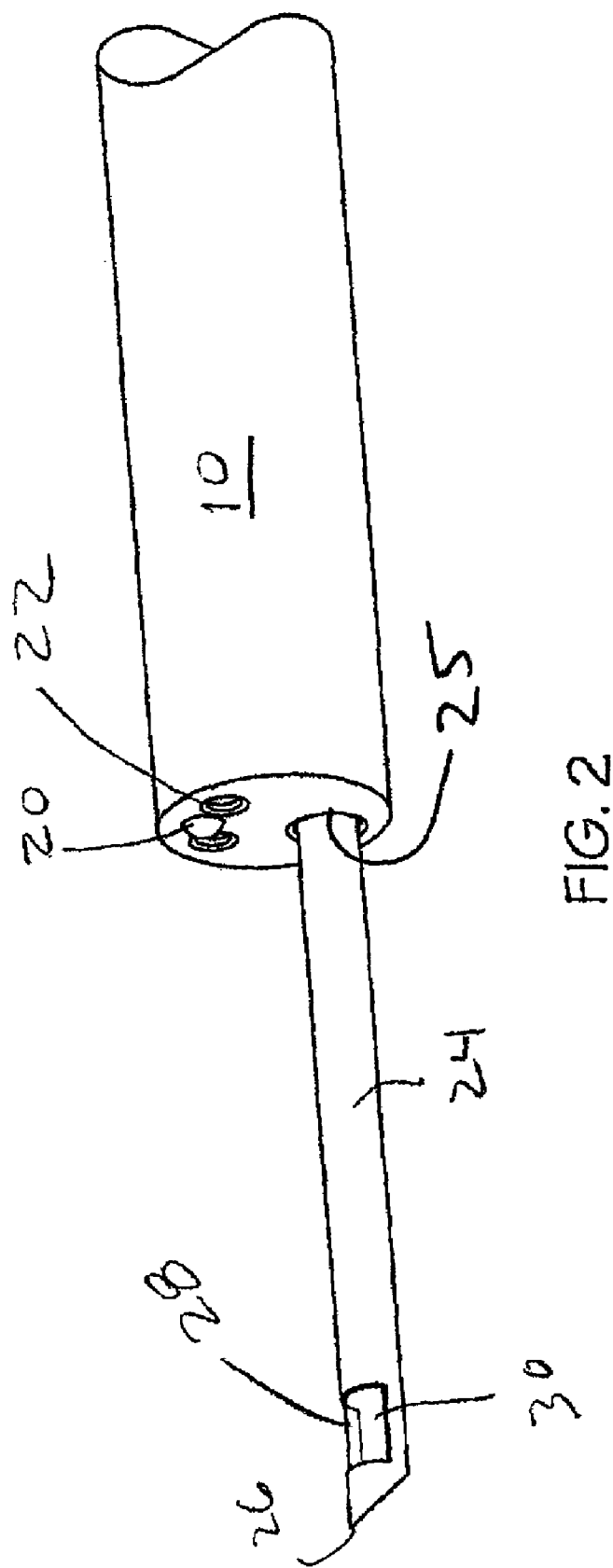
FIG. 2 is a perspective schematic view of the end of the endoscope depicted in FIG. 1 with a mucosal tissue illuminator in accordance with the principles of the present invention extending outwardly from a working channel of the endoscope.

The exemplary embodiment illustrated in the drawing depicts a structure to provide such positional information about the underlying circulatory system. More specifically, FIG. 2 shows the distal end of the endoscope 10 depicted in FIG. 1 with a light probe 24 extending outwardly from its distal end. The illustrated light probe 24 extends through a working channel 25 of the endoscope 10. In the specific form illustrated, the light probe 24 has a generally cylindrical configuration that terminates in a tapered penetrating end tip 26. A light window 28 is provided in a circumferential portion of the probe 24 proximal to the end tip 26. The light window 28 directionalizes light emitted from a light source 30 disposed in the light window 28. The light source 30 may include any of several well-known light emitting devices, such as an optic fiber or a light emitting diode.

It is desirable to position the light source 30 on a side of an area to be examined that is opposite the side where the light detecting sensor 19 is located, and to thereafter direct light emitted from the light source 30 toward the light detecting sensor 19. This may be accomplished by simply positioning the light source 30 on a side of the area to be examined, such as the area adjacent to the eroded portion 12, and detecting the scattered light passing through that area 12 with the light detecting sensor 19. Blood vessels in the mucosal lining 14 provide light scatters so that the pattern of light detected by the light detecting sensor 19 is representational of the positional attributes of the blood vessels and other structures within the mucosal lining 14. For best results, the light source 30 should be placed close enough to the mucosal lining 14 so as to substantially eliminate reflectance of light emitted from the light source 30. Reflectance of the light emitted from light source 30 can be reduced by contacting the mucosal lining 14 with the light source 30, or even more preferably, by pressing a light source 30 against the mucosal lining 14.

Figure 3:
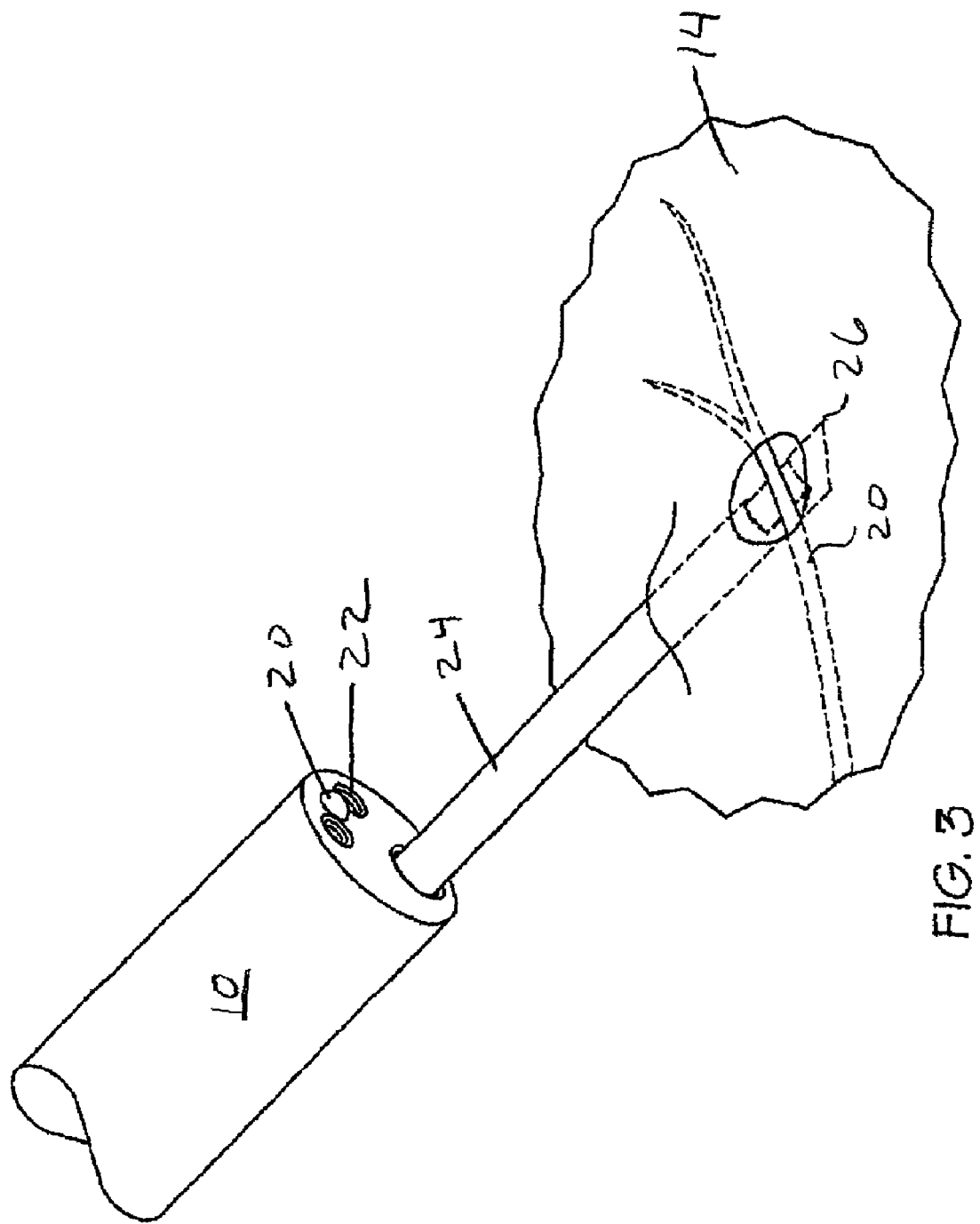
FIG. 3 is a perspective schematic view showing the mucosal tissue illuminator depicted in FIG. 2 positioned beneath the blood vessel shown in FIG. 1 to provide backlighted transillumination of the blood vessel.

The most readily recognizable light pattern might be achieved by penetrating the light source 30 into the mucosal lining 14 on a side of the area being examined that is opposite from light detecting sensor 19. As shown in FIG. 3, the end tip 26 of probe 24 is tapered into a point for easy penetration into the mucosal lining 14 of the stomach. In this depiction, the light emitted from the light source 30 is directionalized by the light window 28 and passed through the eroded area 12 to the light detecting sensor 19. Specifically, the light window 28 is positioned on a side of the eroded area 18 opposite from the side on which the visual light detecting sensor 19 is positioned. With the light window so positioned, light from the light emitting diode 30 is directed through the stomach lining toward the light detecting sensor 19. The patterns of light scattering created by the blood vessel 20 allows the light sensor 19 determine the positional attributes of the structures within the lining 14, including the position of blood vessel 20.

The foregoing description of the preferred embodiments of the present invention have been presented for purposes of illustration and description. It is not intended to be exhaustive or to limit the invention to the precise form disclosed. Obvious modifications or variations are possible in light of the above teachings. For example, the certain aspects of the invention can be used to identify lesions in the mucosa, whether the lesions are benign or cancerous. The embodiments were chosen and described to provide the best illustration of the principles of the invention and its practical application to thereby enable one of ordinary skill in the art to utilize the invention in various embodiments and with various modifications as are suited to the particular use contemplated.

All such modifications and variations are within the scope of the invention as determined by the appended claims when interpreted in accordance with the breadth to which they are fairly, legally and equitably entitled. The drawings and preferred embodiments do not and are not intended to limit the ordinary meaning of the claims in their fair and broad interpretation in any way.

What is claimed is:

1. A method of identifying structures proximal to an area of interest in the stomach, comprising:
   (a) using an endoscope to identify an area of interest in the mucosal lining of a patient's stomach;
   (b) scattering light from a light source into the mucosal lining of the stomach at a location adjacent to, and on a first side of, the identified area;
   (c) positioning a light detector on a second side of the identified area opposite to the first side;
   (d) directing light from the light source into the mucosal lining toward the second side of the identified area;
   (e) using the light detector positioned on the second side of the identified area to detect patterns of light representative of positional attributes of structures within the identified area that are created by light emanating from the light source on the first side of the identified area and scattered in its travel though the mucosal lining; and
   (f) using the detected light patterns to determine positional attributes of the structures within the identified area.

2. A method as recited in claim 1 wherein the step of scattering light includes inserting a light source into the mucosal lining.

3. A method as recited in claim 1 wherein the step of scattering the light includes pressing a light source against the mucosal lining of the stomach.

4. A method as recited in claim 1 wherein the step of scattering the light includes positioning a light source in close proximity to the mucosal lining of the stomach.

5. A method as recited in claim 4 wherein the light source is positioned close enough to the mucosal lining of the stomach to substantially eliminate reflectance of light waves from the light source.

6. A method as recited in claim 1 wherein the area of interest is ulcerated.

7. A method as recited in claim 6 further including the step of treating the ulcerated area.

8. A method as recited in claim 1 wherein the area of interest contains a lesion.

9. A system for visually ascertaining attributes of structures located beneath mucosal linings of the stomach, comprising:
   (a) an elongated shaft, the shaft being configured for passage though a working channel of an endoscope;
   (b) a light source disposed proximal to the end of the elongated shaft, the light source being adapted for contact with mucosal lining of the stomach and capable of directing light with sufficient luminous intensity to pass through mucosal linings of the stomach in a predetermined direction;
   (c) a light detector for detecting scattered patterns of light and producing an image representative of the patterns, the light detector being capable of ascertaining positional attributes of blood circulatory structures within the mucosal lining from the differential intensity of light passing through portions of the mucosal lining from the light source due to attenuation of the light by the circulatory structures.

10. A system as recited in claim 9 wherein the light source is disposed in the shaft, and in the shaft includes a window for directing light emanating from the light source.

11. A system as recited in claim 10 wherein the shaft has a generally cylindrical configuration.

12. A system as recited in claim 11 wherein the window is disposed in the circumferential section of the shaft.

13. A system as recited in claim 11 wherein the window has circumferential edges, and the width of the window between the circumferential edges is less than 50% of the circumference of the shaft.

14. A system as recited in claim 9 wherein the light source includes a light emitting diode.

15. A system as recited in claim 9 wherein the light source includes an optic fiber.

16. A system as recited in claim 9 wherein the light source has an intensity of between 20 lux and 50,000 lux.

17. A system as recited in claim 9 wherein the distal end of the shaft is tapered to facilitate piercing of the mucosal lining.

* * * * *